(12) United States Patent
Bell et al.

(10) Patent No.: US 7,915,901 B2
(45) Date of Patent: Mar. 29, 2011

(54) LOW-PROFILE ELECTRICAL RESISTANCE CORROSION SENSOR

(75) Inventors: Graham E. C. Bell, Claremont, CA (US); Clifford G. Moore, Arcadia, CA (US)

(73) Assignee: M. J. Schiff & Associates, Inc., Claremont, CA (US)

( * ) Notice: Subject to any disclaimer, the term of this patent is extended or adjusted under 35 U.S.C. 154(b) by 461 days.

(21) Appl. No.: 12/024,979

(22) Filed: Feb. 1, 2008

(65) Prior Publication Data
US 2009/0195260 A1 Aug. 6, 2009

(51) Int. Cl.
*G01R 27/08* (2006.01)
(52) U.S. Cl. ...................................................... 324/700
(58) Field of Classification Search .................. 324/700
See application file for complete search history.

(56) References Cited

U.S. PATENT DOCUMENTS

| | | | |
|---|---|---|---|
| 4,338,563 A | 7/1982 | Rhoades et al. | |
| 4,514,681 A | 4/1985 | Finley et al. | |
| 4,587,479 A | 5/1986 | Rhoades et al. | |
| 4,755,744 A | 7/1988 | Moore et al. | |
| 4,839,580 A | 6/1989 | Moore et al. | |
| 5,243,297 A | 9/1993 | Perkins et al. | |
| 5,627,749 A | 5/1997 | Waterman et al. | |
| 5,712,559 A | 1/1998 | Moore et al. | |
| 6,383,451 B1 * | 5/2002 | Kim et al. ....................... | 422/53 |
| 6,919,729 B2 | 7/2005 | Tiefnig | |

OTHER PUBLICATIONS

Rohrback Cosasco Systems, Inc., Model 600, "Corrosometer® Probe Atmospheric", Bulletin # 212-F (2 pgs). Date: Sep. 2004.
Rohrback Cosasco Systems, Inc., Model 610, "High Sensitivity Atmospheric Corrosion Sensor", Bulletin # 213-G (2 pgs). Date: Sep. 2004.
Rohrback Cosasco Systems, Inc., Model 620DI, "Corrosometer® Probes", Bulletin # 216-B (2 pgs). Date: Sep. 2004.
Rohrback Cosasco Systems, Inc., Model 620HD/650, "Corrosometer® Probes", Bulletin # 214-E (2 pgs). Date: Sep. 2004.

* cited by examiner

*Primary Examiner* — Amy He
(74) *Attorney, Agent, or Firm* — Christie, Parker & Hale, LLP (57) ABSTRACT

A thin and narrow electrical resistance corrosion sensor defines measurement, reference and check resistors as abutting serially disposed portions of a thin strip-like metal resistance element, such as a carbon steel or ductile iron element, having metallurgical properties which match those of a corrodible structure of interest such as a pipeline buried in the ground. The resistance element is bonded to a thin, long and narrow nonconductive structural substrate to which is also bonded a flat wire harness which includes conductors connected to the ends of the resistance element and to selected locations of the element between its ends. The resistance element, the substrate, and the wire harness and its connections to the resistance element are encapsulated by a nonconductive protective coating except over the area of the measurement resistor so that such resistor can be exposed to the adjacent environment. The sensor can be used with conventional corrosion measurement instruments. Arrangements for use of plural sensors to measure corrosion due to direct current in a structure of interest, and to measure corrosion due to alternating currents in that structure, also are described.

14 Claims, 5 Drawing Sheets

LOW-PROFILE ELECTRICAL RESISTANCE CORROSION SENSOR

FIELD OF THE INVENTION

The present invention relates to electrical resistance (ER) corrosion sensors. More particularly, it pertains to an ER corrosion sensor which is thin, lies flat and has a small cross-sectional area. It also pertains to the use of such sensors to measure corrosion of a structure of interest due to direct currents, or due to alternating currents, or due to the combined effects of direct and alternating currents. The invention is particularly useful for measuring in situ corrosion of, or the effectiveness of cathodic protection on, ductile iron pipe.

BACKGROUND OF THE INVENTION

Corrosion is the natural process by which metals, due to the environment to which they are exposed, revert to more chemically stable oxides. The more chemically stable oxides are more electrically resistive and do not conduct electrical current as well as the metal. By periodically measuring the change in resistance of a thin strip of metal exposed to the environment, the accumulation of corrosion damage over time, and the rate of corrosion, can be measured; as the metal strip becomes thinner, its resistance increases. The rate of corrosion is dependent on material composition and surface-specific conditions, as well as the level of corrosion protection applied to the metal. An example of a relevant surface specific condition is found in ductile iron pipe where the annealing oxide formed on the pipe surfaces during manufacture of the pipe reduces the rate at which such a pipe corrodes.

Cathodic protection (CP) is a known technique for controlling the corrosion of a metal surface. In this technique, the metal surface is utilized as a cathode of an electrochemical cell. Using CP, metal structures are better protected from corrosion. CP systems are commonly used to protect water and fuel pipelines, storage tanks, steel pier piles, ships, offshore oil platforms, and onshore oil well casings.

A sensor may be used to measure (or monitor) the effectiveness of a CP system when the sensor is applied, for example, to an oil or gas pipeline, to a potable water pipeline, or to a sewer line. Oil and gas pipelines, oil storage tanks, and other similar structures may be made of steel. Water pipelines may be made of ductile iron (DI). DI pipes have non-round cross-sections and have irregularly shaped exterior surfaces defined by the annealing oxide formed as such pipes are manufactured.

Electrical resistance (ER) sensors are known in the art; they are approximately 3 inches long and 1.2 inches wide and have thicknesses in the range of 0.5 to 0.75 inches. A sensor of this type often, if not usually, is connected to a measuring instrument or device via a connecting cable, having a diameter of 0.4 inches, for example. The sensor is secured, as by bonding directly to a DI pipe, and the pipe and the sensor are wrapped or encased with polyethylene or are covered by some other suitable protective material such as a mortar, for the purpose of protecting the pipe (a common structure of interest) from ambient conditions, notably soil.

However, the size of the sensor (as well as the diameter of the connecting cable) can cause the polyethylene wrap to "tent" and thereby provide a path through which groundwater or moisture can penetrate the wrap and make contact with the pipe, thereby defeating the purpose of the wrapping or encasement around the pipeline. In addition, the size of the sensor can limit its applicability to mortar coated pipe joints and in other situations requiring a lower degree of physical interference. A need exists for an improved ER sensor which is of significantly reduced cross-sectional area, i.e., lower profile, and which has a connector cable of reduced cross-sectional area, to enable better isolation of an instrumented pipeline, e.g., from ambient conditions and to enable sensor use in places where existing sensors cannot be used effectively.

While corrosion of pipelines and other structures of interest (SOIs) has long been known to involve the effects of direct currents flowing in the structure, there is a growing concern that alternating currents present in such structures can produce corrosion. Alternating currents can be induced in support towers for electrical power transmission lines and in other structures, such as buried pipelines. A need exists for corrosion sensor arrangements which permit and enable the detection and measurement of corrosion due to the effects of either or both of direct and alternating currents.

Further, existing ER corrosion sensors have inadequate sensitivity for short-term use, such as in the making of measurements for determining proper CP to be applied to a SOI. A need exists for an ER corrosion sensor having increased sensitivity.

SUMMARY OF THE INVENTION

The present invention addresses the needs identified above. The invention provides an ER corrosion sensor arrangement which has a small cross-sectional area and low profile compared to existing ER corrosion sensors. The sensor has materially increased sensitivity. The sensor can be used to measure corrosion of a structure of interest due to alternating currents only, due to direct currents only, and due to the combined effects of alternating and direct currents.

Generally speaking, this invention provides an electrical resistance corrosion sensor assembly which includes an elongate strip-like electrically conductive metal sensor element having selected metallurgical properties. A plurality of insulated wires are provided and respective ones of them are conductively connected to the sensor element at the ends of the element and to measure, common, reference, and check locations serially spaced along the element, and to an additional location which is disposed substantially centrally between the measure and common locations. The assembly includes an elongate electrically nonconductive structural substrate to which the sensor element and the conductor wires are secured with the wires extending from and beyond the substrate. An electrically nonconductive coating material covers and seals the sensor element and the connections of the wires to the element except for the provision through the coating material of an opening to the surface of the element between the common location and the end of the element proximate to the measure location.

Another aspect of the invention provides a system for measuring corrosion in a selected portion of a metal structure of interest. The system comprises a sensor which includes first and second resistors. The first resistor is defined by a metal which has metallurgical properties similar to those of the structure of interest. The second resistor has a selected resistance related to the resistance of the first resistor. The first and second resistors are disposable proximate to the selected portion of the structure of interest with the first resistor metal exposed to the same corrosion environment as the selected portion of the structure of interest and with the second resistor sealed from that environment. Conductors are connected to the first and second resistors and by which a potential can be measured across each of the resistors when a known (or constant) current is caused to flow through the resistors. A circuit which includes a filter for blocking the flow of direct current or the flow of alternating current is establishable between a selected location on the first resistor and the structure of interest.

DESCRIPTION OF THE DRAWINGS

The above-mentioned and other features of the invention are more fully set forth in the following description of presently preferred and other embodiments of the invention, which description is presented with reference to the accompanying drawings in which.

DETAILED DESCRIPTION

The detailed description set forth below in connection with the appended drawings is intended as a description of exemplary embodiments of corrosion sensors and corrosion sensor systems provided in accordance with the present invention and is not intended to represent the only forms in which the present invention may be constructed or utilized. It will be understood, however, that the same or equivalent functions and structures may be accomplished by arrangements that are also intended to be encompassed within the spirit and scope of the invention. In the following descriptions, like reference numbers denote like or similar like elements or features.

Figure 1:
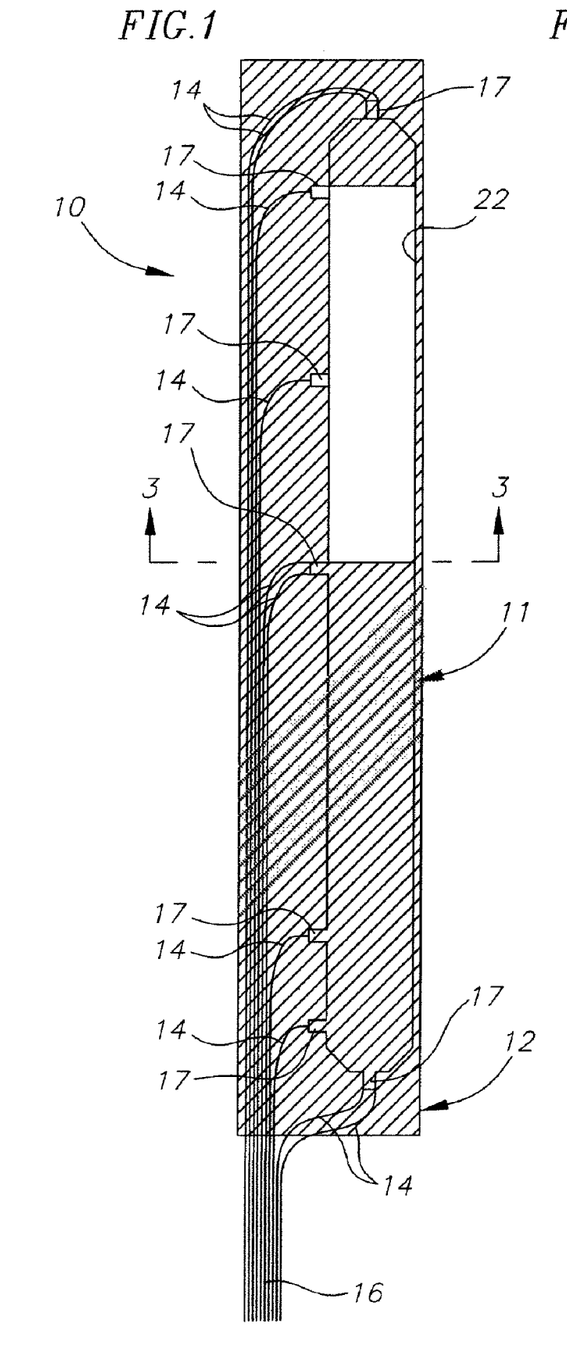
FIG. 1 is a plan view of an electrical resistance corrosion sensor assembly according to the invention.
Figure 2:
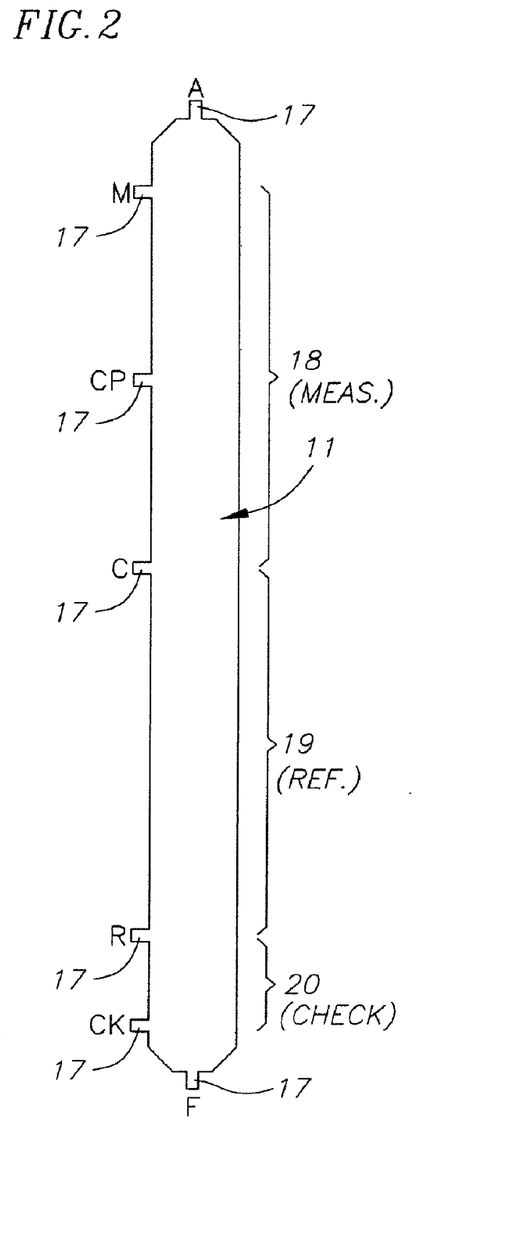
FIG. 2 is a plan view of the resistance element of the assembly shown in FIG. 1.
Figure 3:
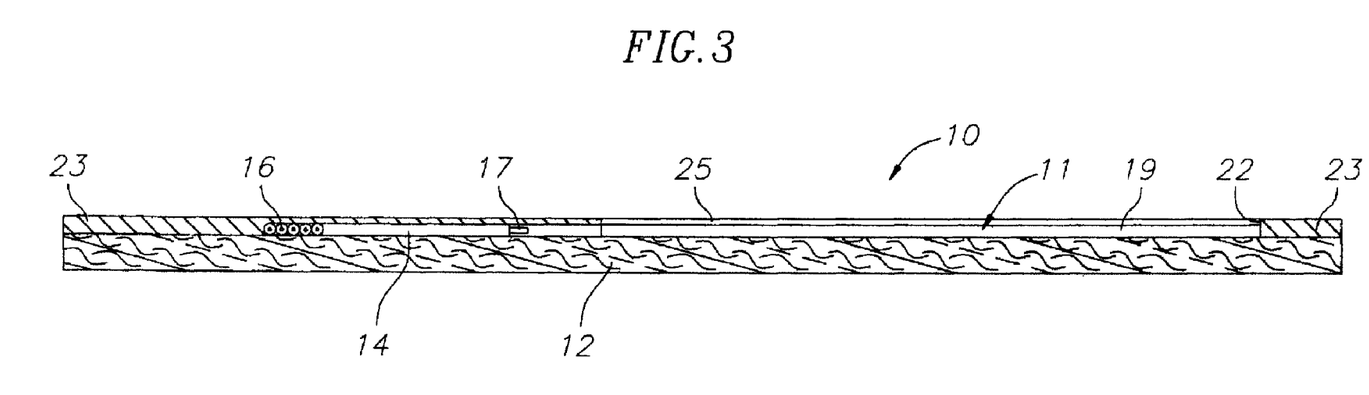
FIG. 3 is a cross-sectional elevation view taken along line 3-3 of FIG. 1.

FIG. 1 of the accompanying drawings is a plan view of a compact, low-profile electrical resistance (ER) corrosion sensor and measurement assembly 10 according to one physical embodiment of this invention. Such assemblies are often called "probes" in the corrosion measurement and prevention industry, and that term is often used herein as a synonym for sensor assembly 10. FIG. 2 is a plan view of a strip-like resistance element 11 which is a principal component of sensor 10. Other components of the sensor, as shown in FIGS. 1 and 3 (the latter being an enlarged transverse cross-section view of the sensor as may be taken along line 3-3 in FIG. 1) are a structural substrate 12, insulated wires 14, and an electrically nonconductive coating material 23 which encloses and seals, with the important exception noted below, the other sensor components in an essentially hermetic manner.

Resistance element 11 is defined by a strip of metal of selected length, width and thickness. The metal used to define the resistance element preferably has metallurgical properties which are the same as, or very similar to, the metallurgical properties of a metal structure of interest (SOI) on, for or in respect to which sensor 10 is to be used to obtain desired measurements of actual or potential corrosion. If the SOI is a steel pipeline, such as one for the transmission of oil or gas, the resistance element 11 for a corrosion sensor 10 useful to measure corrosion of the pipeline, or to make measurements useful to establish the specifics of cathodic protection for corrosion prevention for the pipeline, preferably is defined by the same type of steel (e.g., a carbon steel) used to define the pipe lengths which are connected to form the pipeline. If it is not possible or practical to define the resistance element of a corrosion sensor assembly to have the same metallurgical properties as those of a particular SOI, the metal used to define the sensor resistance element is selected to have chemical properties which are the same as, or very similar to, the chemical properties of the metal of the SOI.

Sensor 10 (FIGS. 1, 2 and 3) is constructed for use in association with a steel SOI, such as a steel pipeline or pipeline formed by lengths of steel-reinforced concrete. Therefore, resistance element 11 is formed of steel. A preferred steel resistance element has a uniform thickness of 0.010 inch (10 mils; 1 mil=0.001 inch), an overall length of 5.5 inches (5.25 inches excluding a ⅛" long connection tab or tap at each end) and a width of 0.50 inches exclusive of connection taps at the side(s) of the resistance element.

Wires 14 preferably are components of a thin, flat multi-wire cable (wire harness) 16, and it is preferred that the flat cable has ten wires. Respective ones of wires 14 preferably are conductively secured, as by welding or soldering, to pertinent ones of several connection tabs 17 which extend from the ends and sides (preferably only one side) of sensor element 11 as shown in FIGS. 1 and 2. The connections to the sensor element's end tabs enable the application of a potential (an AC potential) across the entire element so that current can flow from end to end of the element. Preferably two wires 14 of harness 16 are used to make each sensor element end connection.

It is preferred that, in addition to the taps at the ends of element 11, five further taps are defined at spaced locations along one side edge of the element. For ease of reference in the following descriptions, the preferably seven taps of element 11 are given letter notations in FIG. 2 as follows: A and F at the opposite ends of the element, and M (Measure), CP (Cathodic Protection in most cases), C (Common), R (Reference), and CK (Check) along the side of the element. A respective one of harness wires 14 is connected to each of the M, CP, R and CK taps 17, and two (preferably) harness wires are connected to the C tap.

The connections of wires 14 to the M, C, R and CK taps at the side of sensor element 11 result in the presence in the element of three serially arranged and directly connected resistors 18, 19, and 20. Each resistor is defined by the portion of the element which is between the locations of adjacent ones of the wire connection taps. That is, a measurement (MEAS.) resistor 18 is defined between the M and C taps, a reference (REF.) resistor 19 is defined between the C and R taps, and a check (CHECK) resistor 20 is defined between the R and CK taps.

While the resistors which comprises an ER sensor according to certain system aspects of the invention (see FIG. 6, for example) could be defined by separate electrically resistive devices (one of which having SOI matching metallurgy) wired together in a preferably serial relation, the definition of those resistors as serially aligned abutting portions of a single thin metal strip-like element is preferred according to the sensor (probe) aspects of the invention illustrated in FIGS.

1-4. The latter arrangement is preferred so that a small, thin and compact sensor assembly is provided. Also, according to the sensor aspect of the invention, it is preferred that the resistance values (ohms) of resistors 18 and 19 are equal, and the resistance value of resistor 20 is a selected fraction of the value of resistor 19. It is preferred that resistance 20 is ¼ that of resistance 19.

An initial step in the manufacture of probe 10 is the connection of the wires 14 of flat cable harness 16 to the correct ones of sensor element tabs 17. Then the sensor element and the harness are bonded to substrate 12. The preferred substrate is a one inch by six inch piece of G10/FR4 Garolite epoxy impregnated fiberglass sheet having a thickness of about 0.031 inch. Care is taken to assure that the nonconductive bonding agent is present in all locations between the sensor element and the substrate. Duralco 4525 epoxy is a suitable bonding agent. Thereafter, as shown in FIGS. 1 and 3, the sensor element 11 and attached wires, as secured to the substrate, are coated and sealed (encapsulated) by a suitable material 23, such as by use of Duralco 4525 epoxy, except as to the area of sensor element 11 which defines the measurement resistor 18. That is, the encapsulating material 23 is applied to the combined sensor element and substrate so that an opening 22 is formed through the encapsulation 23 to the upper surface, preferably the whole of the upper surface, of resistor 18. The top surface 25 (FIG. 3) of probe 10, as defined by encapsulation 23, is spaced above the top surface of sensor element 11 by a distance of about 0.01 inch. If desired, the encapsulating material can form a thin layer over the sides, ends and bottom surface of substrate 12.

The preferred overall thickness of probe 10 is nominally 0.050 inch, i.e., in the range of from about 0.045 inch to 0.055 inch.

Flat cable 16 extends from the probe, preferably from one end of the probe, for a desired distance, say about 12 to 15 feet, to a hermetically sealed connection 26 where a transition is made from the flat cable to a round cable 27 which has one conductor for each wire of the flat cable. Connection 26 preferably is made by splicing of conductors of harness 16 to those of cable 27. The round cable preferably is more robust than the flat cable which, with connection 26, typically is buried in the ground with the structure of interest. Round cable 27 can be armored if desired and is of desired length. At its end opposite from probe 10, the conductors of the round cable, with the preferred exception of the conductor connected at connection 26 to wire 14 which extends to the probe's CP tap, to respective terminals of a termination connector 28 (see FIG. 6, e.g.). Connector 28 preferably conforms to U.S. military specifications for ruggedness and reliability and is configured to mate with an input connector of standard configuration which is a component of an existing corrosion measurement instrument, of which there are several, such as a Corrosometer® instrument made by Rohrback Cosasco Systems, Inc., Santa Fe Springs, Calif. The round cable conductor which is associated with the probe's CP tap preferably is connected within the housing of termination connector 28 to a wire which extends from the rear end of that housing to define a pigtail lead 29 for use, as desired, as described below.

Figure 4:
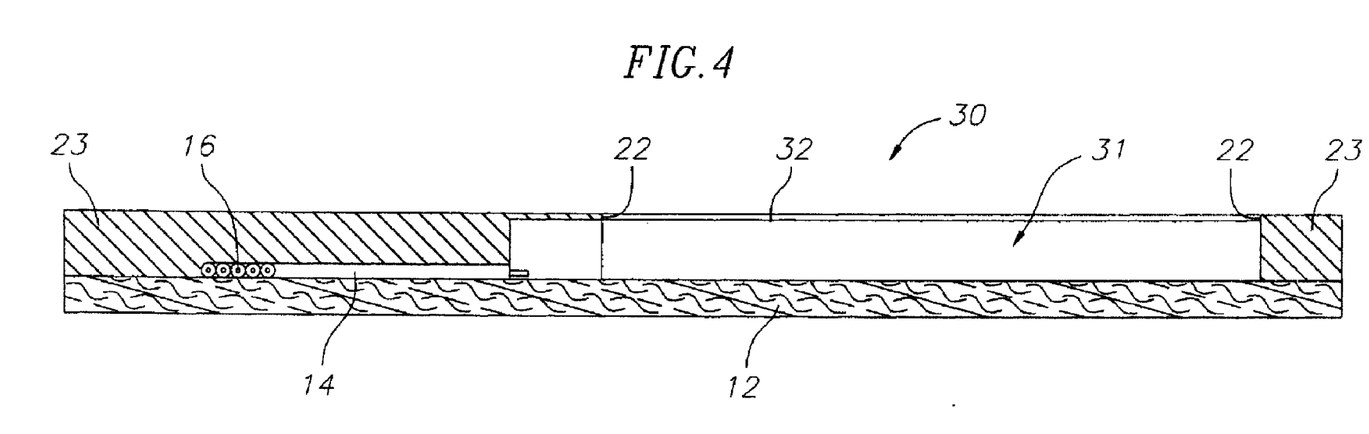
FIG. 4 is a cross-sectional view similar to FIG. 3 but depicting aspects of another sensor assembly according to the invention.

Another sensor assembly (probe) 30 according to this invention is shown in the cross-sectional elevation view of FIG. 4. Probe 30 is constructed for use with a structure of interest which is made of ductile iron pipe. Probe 30 is defined consistently with the preceding description of probe 10 except as to its resistance element 31 in view of the preference that a probe assembly according to this invention includes a resistance element having metallurgical properties like or similar to the metallurgical properties of a structure of interest. That is, probe 30 is like probe 10 except that probe 30 includes a resistance element 31 defined by ductile iron rather than by steel, and except for aspects of element 31 which are related to the material of the element.

Ductile iron resistance element 31 preferably has the same plan shape and plan dimensions as does steel resistance element 11 depicted in FIG. 2. Thus, resistance element 31 has wire connection tabs (taps) 17 at each of its ends, and five taps 17 along one side, those taps being denoted as A, M, CP, C, R, CK and F with taps M, C, R and CK being located at the ends of three resistors 18 (denoted MEAS. REF., and CHECK) defined by the element. However, as shown by the differences between FIGS. 3 and 4, ductile iron element 31 can be, and typically is, of greater thickness than is element 11. That greater thickness can be a manifestation of the well-known difficult machinability of ductile iron. It is preferred that element 31 be fabricated from a piece (coupon) of ductile iron cut from an exterior portion of a length of ductile iron pipe so that the pipe exterior surface is present in element 31 as the top surface 32 of the finished element as secured to substrate 12 in probe 30. It is also preferred that the diameter of the ductile iron pipe from which that coupon is obtained be of sufficient diameter that the curvature of the element's top surface is negligible.

Ductile iron pipe is manufactured in discrete lengths by a spin casting process. An artifact of that process is that the exterior surface of such a pipe as cast has a pebbled surface, i.e., a non-smooth surface. A further step in the manufacture of ductile iron pipe is annealing of the cast pipe lengths. An artifact of the annealing process is that the surfaces of the pipe are covered by an annealing oxide which is a nonconductive dielectric in its own right. The annealing oxide on the pipe surface makes the ductile iron more resistant to corrosion than ductile iron which does not have such an oxide coating. A typical intended use of ductile iron probe 30 is the application of the probe to an exterior surface of a ductile iron pipeline as the pipeline is being installed. Thus, the presence of the annealing oxide on the exposed surface of the MEAS. resistor 18 part of element 31 as incorporated into probe 30 enables the probe to closely emulate a newly laid ductile iron pipe line and to respond to the environment of the pipeline in the same manner as the pipeline responds to that environment.

It was noted above that it is preferred that the measurement resistance 18 and the reference resistance 19 be defined by the same material and have equal cross-sectional areas and lengths. Those properties of resistors 18 and 19 provide inherent first order temperature compensation in probes 10 and 30 when corrosion measurements are made by use of the probes. Also, those resistances are provided by conductive materials which have relatively high resistivity so that the desired minimum resistance values (1 mill ohm for the measurement resistor) required for acceptable probe sensitivity can be attained in a compact structure. Compactness, in this instance, means short, narrow, and thin. A short and narrow probe can be used in a broadened range of situations, and a thin probe is one which can be mounted to a pipeline, e.g., under a protective wrap or encasement of the pipeline with reduced likelihood that the presence of the probe will be a cause of leaks in the wrap or encasement. The flat and thin nature of the electrical cable extending directly from the probe also contributes to the prevention of leaks through pipeline wraps or encasements, e.g.; connections 26 between flat cables 16 and round cables 27 are spaced sufficiently from the probes that those connections are outside any relevant pipeline wraps or encasements.

A measurement of corrosion is obtainable from the ratio of the resistance of the measurement resistor 18 to the resistance of the reference resistor 19 which is protected from the environment of the probe. Under conditions in which the material of the measurement resistor is caused to become corroded, the thickness of the cross-section of the resistor is reduced, and the ratio increases due to the reduced cross-section of the resistor. In contrast, it may be assumed that the ratio is unaffected by temperature changes because the respective resistances of both of resistors 18 and 19 will increase or decrease by approximately equal percentages due to changes in temperature.

ER probes and related instrumentation determine metal loss (as caused by, for example, corrosion) by measuring the increase in resistance of a given piece of material as its cross-sectional area is reduced by reason of metal loss due to corrosion. The corrosion rate can be determined by dividing the change in metal loss at any two measurements by the time separating the two measurements, i.e., the corrosion rate is the slope of a curve representing actual metal loss. These types of measurements can be used in virtually any environment, e.g., gaseous, liquid or buried.

The electrical resistance of a piece of electrically conductive material such as a metal may be expressed by the formula $R=\rho L/A$, where $\rho$ is the electrical resistivity of the material, L is the length of the piece of material, and A is the cross-sectional area of the piece of material. The electrical resistivity $\rho$ may vary between different materials and may be a function of temperature. For a given material at a constant temperature, the electrical resistance of a fixed-length sample increases as its cross-sectional area decreases. A measurement of resistance change of a corrodible metal may be used to determine (or estimate) a corresponding amount of metal loss due to corrosion.

As also explained previously, compensation for change of resistivity ($\rho$) with temperature is provided by reference resistor 19 which is protected from the corrosion process (e.g., via the protective coating). As the electrical resistance of the resistor 18 increases with temperature, the electrical resistance of the reference resistor 19 also increases. However, the ratio of the resistances remains substantially unchanged due to temperature effects. That is, the ratio of the resistance of the MEAS. resistor 18 ($R_M$) to the resistance of the REF. resistor ($R_R$) increases only when the MEAS. resistor's material is caused to become corroded.

Since ER sensor elements have lower (or much lower) electrical resistances than connecting cables and connectors, separate conductors (e.g., wires) are used to apply current to the elements and to provide voltage-drop measurements across the MEAS. resistance element 18 and across the REF. resistance element 19. The ratio of the respective resistances is determined by measuring the voltage-drop ratio of the MEAS. and REF. elements 18 and 19 when a constant current is passed through both elements. In more detail, when a current flows across both the MEAS. element 18 and the REF. element 19, the ratio of the voltage drops across the two elements $V_M/V_R$ is equal to the ratio of the resistances $R_M/R_R$.

In light of the increasing resistance of the measurement resistor 18 as it becomes thinner due to corrosion, the span (or useful life) of sensor 10 or 30 is typically related to one-half the thickness of the sensor as it was manufactured. This is a standard convention used for commercial ER probe instrumentation because, once the measurement resistance has lost about one-half of its original thickness, the variation of resistance due to corrosion will become increasingly nonlinear.

In some commercially available ER sensors, an additional resistive element, i.e., the CHECK resistor element is also provided. With reference to FIG. 2, the CHECK element 20 is located and extends between the REF resistor 19 and the adjacent end of the sensor's resistance element 11. In one embodiment of the invention, the resistance of the CHECK element 20 is defined to be one-quarter (¼) the resistance of the REF. resistor 19. To determine one measure of the integrity of the sensor, a ratiometric measurement of the resistance of the REF resistor to the combined resistances of the REF. and CHECK resistor is made. This ratio should, by design, be very close to 0.8 and should not substantially change throughout the service life of the sensor. If, for any reason, there is damage to the sensor or if corrosion occurs on the REF. resistor, this ratio will change and may be an indication of a failed sensor.

Figure 5:
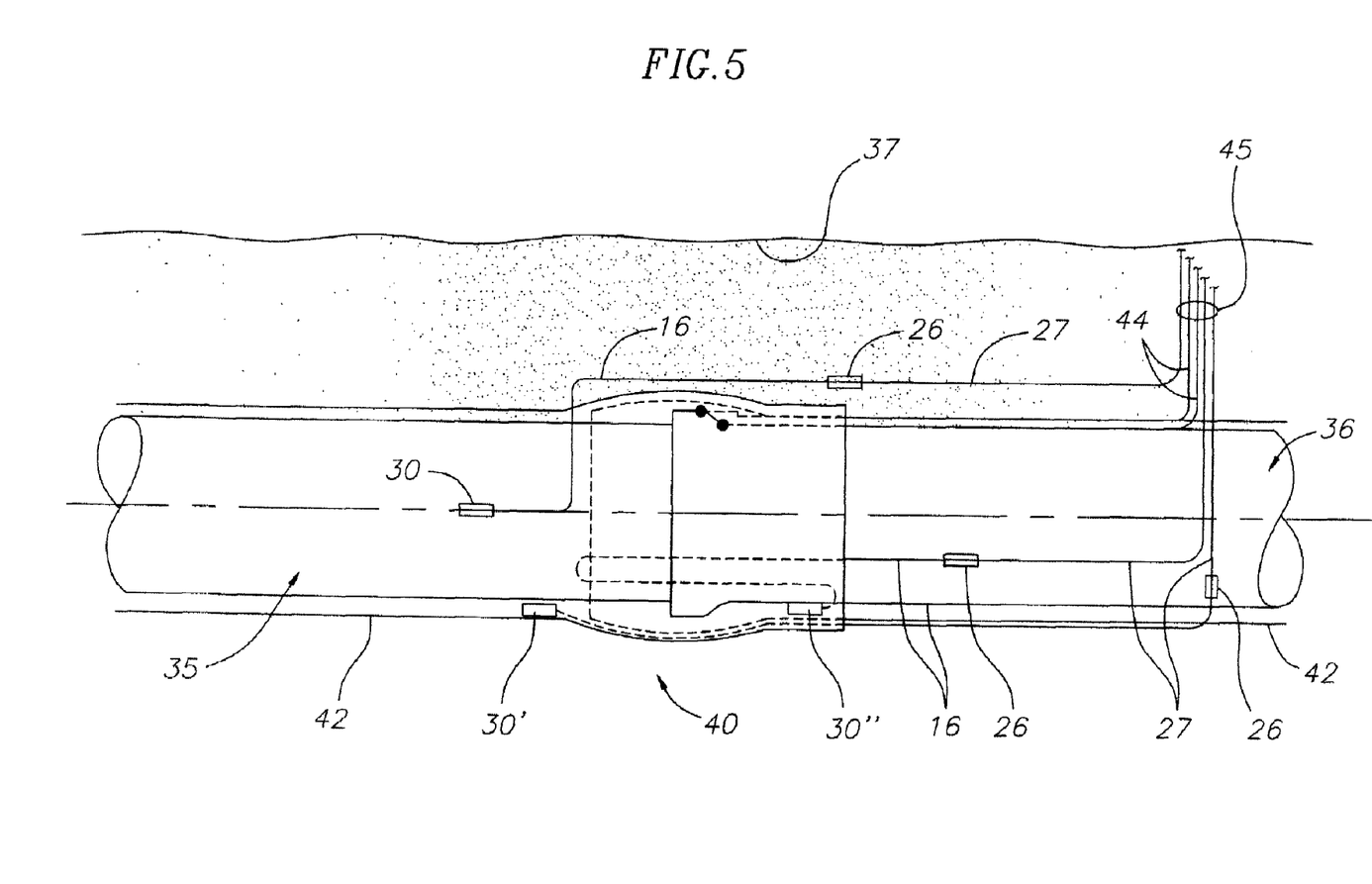
FIG. 5 is a plan view showing the application of three sensor assemblies of the kind shown in FIG. 4 to a buried ductile iron water pipe.
Figure 6:
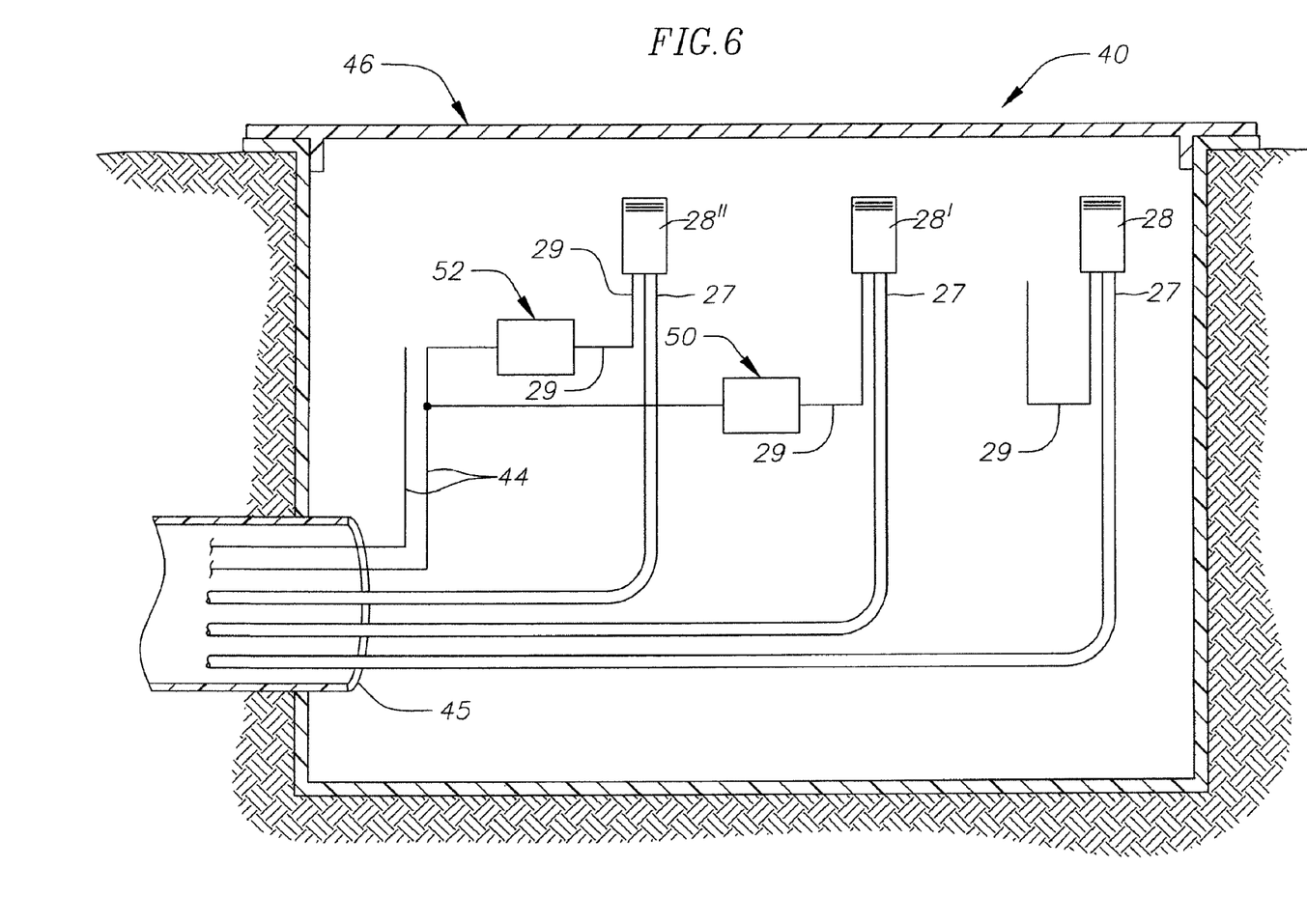
FIG. 6 is a fragmentary schematic diagram depicting how an installation of sensor assemblies as shown in FIG. 5 can be used to measure pipe corrosion due to direct currents and pipe corrosion due to alternating currents.

FIG. 5 is a top plan view of a connection between two lengths 35 and 36 of ductile iron pipe as the pipe lengths which are used to define a portion of a pipeline being laid in a trench 37 in soil or other earth formation. FIG. 5 depicts a common way in which ER corrosion probes are installed on ductile iron pipelines in the course of construction of such pipelines. Consistent with that practice, three ductile iron corrosion sensors 30, 30' and 30" are present at an instrumentation station 40 at a desired location along the pipeline; the spacing between such stations commonly is about 1000 feet. FIG. 5 depicts the below ground aspects of station 40, whereas FIG. 6 depicts aspects of the above ground portion of the station.

As depicted in FIG. 5, one end of each length of pipe is flared outwardly to define a cylindrical sleeve into which the unflared end of an adjacent length of pipe can be inserted and sealed as is well known. The flared end structure of a pipe length is known as a "bell" and the unflared end of the length is known as a "spigot." As delivered to the site of trench 37, each length of ductile iron pipe has loosely disposed around it a sleeve 42 of polyethylene film of desired thickness; the sleeve is bunched on the pipe length as delivered so that the bell and spigot ends of each length are exposed. The overall length of each polyethylene sleeve is greater than the distance between the ends of the pipe length around which the film sleeve is disposed, so that the sleeves later can be disposed in overlapping relation to each other at the sleeve ends across each bell and spigot connection in the pipeline. See FIG. 5.

Most ductile iron and steel pipelines are protected from corrosion by cathodic protection techniques. Cathodic protection is applied to pipelines at regular intervals along the pipeline. Therefore, in the course of installation of a ductile iron pipeline such as that shown in FIG. 5, at each connection between adjacent pipe lengths, a copper strap or jumper wire (not shown) is disposed across the connection and welded, e.g., to the adjacent pipes at the strap ends to assure electrical continuity across the pipeline connection.

Referring again to FIG. 5, three ductile iron sensors 30, 30' and 30" can be components of instrumentation station 40. Sensors 30' and 30" are affixed, as by an adhesive, to the pipeline at the station, preferably on opposite sides of the bell and spigot connections of pipe lengths 35 and 36 and preferably along the sides of the pipeline in a horizontal diametral plane of the pipeline. The encasing polyethylene sleeves are then caused to be in overlapping relation across the pipeline connection and, in the course of that process, the flat cable harness 16 from each of probes 30' and 30" are lead out through the sleeve overlaps to the exterior of the sleeve. The edge of the outer sleeve 42 is then sealed, as by taping to the exterior of the other sleeve circumferentially of the pipeline. In that way, the probes 30' and 30" are sealed from the exterior of the encased pipeline; the thin flat nature of each probe wire harness 16 enables that seal to be made effectively.

Also, before sleeves 42 are sealed together as described above, two (preferably) conductors 44 are conductively connected, as by welding, to the exterior of the pipeline at station 40. Those conductors can be number 12 wires and they are lead out through the overlapping ends of sleeves 42 to the exterior of the encased pipeline. Conductors 44 are redundant and are provided at station 40 so that measurements of pipeline potential can be made using a copper/copper sulfate reference cell.

After sleeves 42 have been overlapped and sealed at station 40, probe 30 is affixed to the exterior of the sleeving at the station. Sealed connections 26 of probe wire harnesses 16 to cables 27 can then be made. Conductors 44 and cables 27 can then be introduced into a suitable conduit 45 which extends from the underground aspects of station 40 to its above ground portion which can be a weatherproof box 46 located in the ground with its openable top substantially flush with the ground surface adjacent to the centerline of the pipeline (see FIG. 6). It is in that box where termination connectors 28 and pigtail leads 29 can be located for access at suitable times.

It will be seen that probe 30 at station 40 is exposed to the environment in the buried location of the pipeline and so can be used to monitor the native corrosion conditions at station 40. Probes 30' and 30", being located inside the overlapped and sealed pipeline encasing sleeves 42, can be used to monitor corrosion of the pipeline since each of those sensors can function as a proxy for the pipeline.

The equivalent of a ductile iron pipe instrumentation station 40 can be defined in the course of the construction of a steel pipeline. Steel pipelines are defined by butt welding together adjacent ends of individual pipe lengths, and then helically wrapping in an overlapping manner the exterior of the pipe with a suitable strip of dielectric protective material after application of a suitable mastic to the exterior of the pipeline. The flat wire harnesses from probes 10 affixed to the pipeline can be lead to the exterior of the encased pipeline between turns of the protective material as it is applied. The balance of an instrumentation situation can then be defined as described above.

FIG. 6 is a fragmentary schematic diagram of the components of instrumentation station 40 which are accessible at an above-ground location. Termination connectors 28, 28' and 28" are associated with probes 30, 30' and 30" respectively. A suitable corrosion measurement instrument can be coupled to any of probes 30, 30' and 30" via connectors 28, 28' and 28" as described above. Probe 30 can be accessed via connector 28 to measure the corrosion which probe 30 experiences under a native corrosion environment. Probes 30' and 30" reflect the actual corrosion environment of the pipeline as encased by protective sleeves 42 at station 40, and so corrosion measurements obtained via connectors 28' and 28" provide information about actual corrosion of the pipeline in that locally protected environment; such measurements also provide information about the integrity and effectiveness of the pipeline's encasement.

Corrosion measurements obtained via connectors 28' and 28" in the period following installation of a pipeline can be used to define the parameters of cathodic protection for the pipeline. That is, initial measurements of actual pipeline corrosion as to amount and rate enable a determination of the value of cathodic protection current to be applied to the pipeline to protect it from further corrosion, or to enable adjustments to be made to cathodic protection during the life of a pipeline. Once cathodic protection of a pipeline has been commenced, the pigtail leads 29 of connectors 28' and 28" can be connected to one or both of conductors 44 so that the measurement resistors 18 of probes 30' and 30" are conductively connected to the pipeline and so act as proxies for the cathodically protected pipeline. They can act as such proxies because cathodic protection currents are applied to them via their central CP taps.

Figure 7:
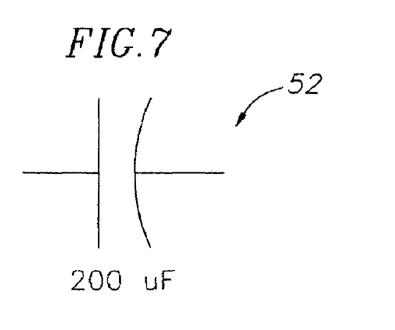
FIG. 7 is a schematic diagram of a filter useful to block direct current flow in a sensor assembly.
Figure 8:
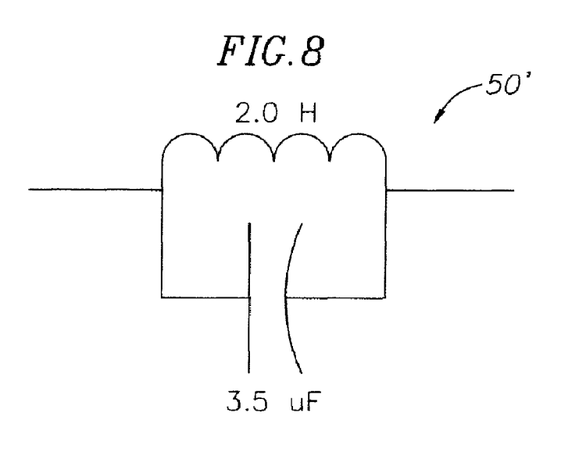
FIG. 8 is a schematic diagram of a filter useful to block the flow of 60 cycle alternating current in a sensor assembly.
Figure 9:
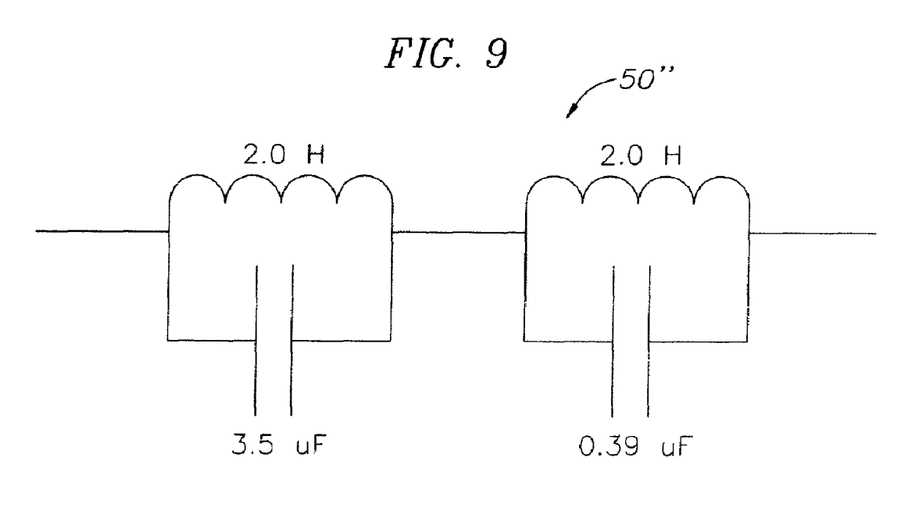
FIG. 9 is a schematic diagram of a filter useful to block the flow of two different frequencies of alternating current in a sensor assembly.

FIG. 6, in combination with FIG. 7-9, illustrates the use of probes 30' and 30" to measure corrosion of the pipeline at station 40 due to direct current (DC) in the pipeline separately from measurement of corrosion in the pipeline at the station due to alternating current (AC) in the pipeline. A DC pass filter 50, which passes direct current and blocks the flow of AC, can be installed in the connection of the pigtail lead 29 from connector 28' to the conductor 44 which connects to the pipeline at station 40. Filter 50 is a long term (permanent) component of the wiring of probe 30' since connector 28' can be used to measure pipeline corrosion due only to DC current in the pipeline. A suitable DC pass filter 50' for blocking single phase 60 Hz. AC current is depicted in FIG. 8, and a suitable DC pass filter 50" for blocking single phase and three phase 60 Hz. AC current is depicted in FIG. 9. Similarly, connector 28" can be used to obtain measurements of pipeline corrosion due to the effects of AC in the pipeline by making an AC pass filter 52 a part of the long term connection of connector 28" to the pipeline via that connector's pigtail lead 29 and conductor 44. A suitable AC pass filter 52 is shown in FIG. 7.

If three probes 10 or 30 are included in an instrumentation station at a pipeline (or other SOI) within the actual corrosion environment with the CP taps of their measurement resistors 18 coupled to the pipeline (or SOI) via the associated pigtail connectors 29 and a return conductor 44, then LPR (linear polarization resistance), EN (electrochemical noise) and EIS (electrochemical impedance spectroscopy) techniques and instruments can be used concurrently to obtain an essentially instantaneous measure of real-time corrosion at the station in the pipeline (or SOI). In each instance, the measure element 18 of the probe serves as the respective electrode. Two probes, such as probes 30' and 30" of station 40, can be used to make the same measurements, but not simultaneously; two measurement events using the two probes would be needed to get the desired LPR, EN and EIS values for useful results.

Some water or sewage pipelines are constructed using steel pipe to which mortar has been applied under factory conditions to the pipe lengths except at their bell and spigot end features. In the course of assembly of such pipe lengths to define a pipeline, mortar is field-applied to the bell and spigot features after those pipe length connections have been made. The field application of mortar to an assembled bell and spigot connection is made by securing a sleeve of film or fabric to the previously applied mortar protective coatings on either side of the pipeline connection, and then introducing mortar into the sleeve so that the pipeline connection is encased circumferentrically in field applied cement. The mortar applied to the pipeline lengths under factory conditions is applied in comparatively dry form which cures to form a comparatively non-porous coating over the major central portion of the pipe length. However, to assure flowability of the mortar applied in the field during construction of a pipeline, the mortar is applied in a comparatively wet form which cures to a comparatively porous state. Therefore, corrosion tends to occur most readily at the bell and spigot connections of such mortar encased pipelines where water is made likely to reach the pipeline metal through the encasement.

A probe 30 according to this invention, due to its geometry and small size, can conveniently and readily be applied to the end face of a pipe length spigot before field application of cement around the completed bell and spigot connection, and its wire harness 16 lead away from the probe, without interfering with the field application of cement to the pipeline connection. That probe can then be used to monitor corrosion at that bell and spigot connection.

Workers skilled in the art to which the foregoing description pertains will appreciate that alterations or modifications of the structures and procedures described above can be made without departing from the inventive scope of the invention as described. Such workers will appreciate that the foregoing description is not intended to be, nor should it be read as, an exhaustive catalog of all of the structural and procedural ways in which the invention can be practiced. The following claims are to be understood and interpreted in that light.

What is claimed is:

1. An electrical resistance corrosion sensor assembly comprising:
   an elongate strip-like electrically conductive metal sensor element having selected metallurgical properties;
   a plurality of insulated wires respective ones of which are conductively connected to the sensor element at connection locations of the element at a first end of the element, a measure location, a location disposed substantially centrally between the measure location and a common location, the common location, a reference location, a check location, and a second end of the element, the connection locations serially spaced along the element;
   an elongate electrically nonconductive structural substrate to which the sensor element and the conductor wires are secured with the wires extending from and beyond the substrate;
   and an electrically nonconductive coating material covering and sealing the sensor element and the connections of the wires to the element except for the provision through the coating material of an opening to the surface of the element disposed between the common location and the first end of the element.

2. A sensor assembly according to claim 1 in which the assembly is useful in association with a corrodable structure of interest and the metallurgical properties of the sensor element and the structure of interest are substantially the same.

3. A sensor assembly according to claim 2 in which the sensor element has substantially a uniform cross-sectional area along its length between the measure and check locations.

4. A sensor assembly according to claim 3 in which the portions of the sensor element between the measure and common locations, between the common and reference locations, and between the reference and check locations respectively comprise measure, reference and check resistors, and the resistances of the measure and reference resistors are substantially the same.

5. A sensor assembly according to claim 4 in which the resistance of the check resistor is less than the resistance of the reference resistor and is a selected fraction of the resistance of the reference resistor.

6. A sensor assembly according to claim 5 in which the resistance of the check resistor is one-fourth the resistance of the reference resistor.

7. A sensor assembly according to claim 1 in which the metal comprising the sensor element is a steel having the selected metallurgical properties and the nominal thickness of the assembly is about 0.05 inch.

8. A sensor assembly according to claim 1 in which the metal comprising the sensor element is ductile iron and the nominal thickness of the assembly is about 0.10 inch.

9. A sensor assembly according to claim 8 in which the ductile iron is in the form of a strip obtained from a ductile iron pipe and includes an exterior surface of the pipe as the surface of the first resistance exposed to the exterior of the assembly.

10. A sensor assembly according to claim 1 in which the insulated wires are components of a flat multi-wire harness which extends a selected distance from the substrate to an end at which the harness wires are connected to respective conductors of a round multi-conductor cable at a first end of the round cable, the round cable extending to an opposite second end where, with the exception of a one cable conductor connected to the harness wire connected to the connection location of the sensor element disposed substantially centrally between the measure and common locations, the cable conductors are connected to terminals carried in a body of an electrical connector.

11. The sensor assembly according to claim 10 in which, at the connector, the end of the one cable conductor is coupled to a free wire which extends from the connector separately from the cable to an end.

12. The sensor assembly according to claim 11 in which the end of the free wire is coupled to a terminal of a filter defined for blocking the flow of either direct current or alternating current.

13. A sensor assembly according to claim 1 in which the sensor assembly is configured to lay flush on a pipeline along the elongate direction of the substrate.

14. A sensor assembly according to claim 13 in which the wires are components of a thin, flat multi-wire cable and are connected to a round cable at a location spaced apart from the substrate and the sensor element.

* * * * *